US00PP18263P2

(12) United States Plant Patent
Bremner

(10) Patent No.: US PP18,263 P2
(45) Date of Patent: Dec. 4, 2007

(54) ***GERANIUM* PLANT NAMED 'ORKNEY CHERRY'**

(50) Latin Name: *Geranium*
Varietal Denomination: ORKNEY CHERRY

(76) Inventor: Alan Bremner, Bendigo St. Ola, Kirkwell (GB), KW15 1SX ( * ) Notice: Subject to any disclaimer, the term of this patent is extended or adjusted under 35 U.S.C. 154(b) by 65 days.

(21) Appl. No.: 11/441,667

(22) Filed: May 25, 2006

(51) Int. Cl.
*A01H 5/00* (2006.01)

(52) U.S. Cl. ..... Plt./329

(58) Field of Classification Search ..... Plt./329
See application file for complete search history.

*Primary Examiner*—Kent Bell
*Assistant Examiner*—Annette H Para

(57) ABSTRACT

A new cultivar of *Geranium* plant named 'ORKNEY CHERRY' that is characterized by low compact spreading habit, dark purple-green foliage, and bright fushsia-red flowers. In combination these traits set 'ORKNEY CHERRY' apart from all other varieties of *Geranium* known to the inventor.

2 Drawing Sheets

Genus: *Geranium* Species ×*hybrida*.
Denomination: 'ORKNEY CHERRY'.

BACKGROUND OF THE INVENTION

The present invention relates to a new and distinct cultivar of cranesbill plant grown as an ornamental for use in border, rock garden, container, or groundcover for the landscape. The new variety is known botanically as *Geranium*×*hybrida* and will be referred to hereinafter by the cultivar name 'ORKNEY CHERRY'.

The new *Geranium* variety named 'ORKNEY CHERRY' is the product of a formal breeding program established by the inventor in 1985 at the inventor's nursery in Kirkwall, Orkney, United Kingdom. The purpose of the breeding program was to identify scientific connections between species of *Geranium,* and to produce new and interesting garden worthy plants with unusual combinations of characteristics. Two new varieties that resulted from this breeding program are *Geranium* 'Sabani Blue' (U.S. Plant Pat. No. 16,305) and *Geranium* 'Westray' (U.S. Plant Pat. No. 13,716).

'ORKNEY CHERRY' is a seedling selection arising from the inventor's controlled cross-pollination of an unnamed seedling of *Geranium*×*antipodeum* as the female parent, and an unnamed seedling of *Geranium*× *oxonianum* as the male parent.

*Geranium*×*antipodeum* is the taxonomic name accorded to hybrids between *Geranium traversii* and *Geranium sessiliflorum.* The derivation of the particular plant of *Geranium*×*antipodeum* used by the inventor is described herein.

*Geranium*×*oxonianum* is itself a hybrid from the cross between *Geranium endressii* and *Geranium versicolor.*

The breeding process which produced 'ORKNEY CHERRY' proceeded as follows:

First, in 1992, the inventor successfully cross-pollinated a plant of *Geranium sessiliflorum* 'Porters Pass' (seed parent, unpatented) with a plant of the species *Geranium*×*traversii* (pollen parent, unpatented). The resulting seed was germinated in 1993, then flowered in 1994 and an individual seedling was selected in 1994 for further hybridization.

Second, in 1995, the individual seedling selected from the foregoing cross was used as seed parent and backcrossed with a plant of *Geranium sessiliflorum* 'Porters Pass' as pollen parent. The resulting seed was germinated in 1996, followed by flowering and selection of a single promising seedling in 1997.

Finally, in 1997, the single promising seedling as above was used as seed parent and crossed with an individual plant of *Geranium oxonianum* (pollen parent, unpatented). The resulting seed was germinated in 1998, then flowered in 1999. The inventor selected an individual seedling, 'ORKNEY CHERRY' from this group of flowering seedlings.

During the breeding process, the flowers of each seed parent were emasculated at the early head stage to prevent self-pollination; which is a problem of small-flowered species, and bagged to prevent cross-pollination. Flowers were collected in the early morning and checked with a lens to ensure that the pollen had not been disturbed. The flowers were kept in a warm room free from pollinators, and the anthers would release the pollen later in the day. The female flower was checked with a lens to ensure that no pollen had been left during emasculation, and was then pollinated with pollen from the male flower — which had been checked with a lens to ensure the pollen was undisturbed. The glassine bag was replaced and remained in place until the seed was collected, or the cross was determined unsuccessful.

The female parent of 'ORKNEY CHERRY' no longer survives, but was a low-growing plant with dark brown leaves and small white flowers. 'ORKNEY CHERRY' is distinguishable from the female parent by greater spreading of habit, leaf colour, leaf shape, flower colour and flower size.

The male parent of 'ORKNEY CHERRY', *Geranium oxonianum,* exhibits small bushy clumping habit, green leaves, and medium-sized reddish-purple funnel-shaped flowers. 'ORKNEY CHERRY' is distinguishable from the male parent by habit, leaf color, flower color, and flower size.

'ORKNEY CHERRY' was selected by the inventor in 1999. Selection was based on a combination of plant habit, leaf size, leaf shape, leaf color, and flower color. 'ORKNEY CHERRY' is characterized by compact low spreading habit, large dark purple-green leaves, and large bright fuchsia-red flowers. Cultural requirements are freely-draining soil, full sun and adequate but not excess water. 'ORKNEY CHERRY' is hardy to USDA Zone 5.

'ORKNEY CHERRY' was first asexually propagated in 2000 in Orkney, United Kingdom. Asexual propagation was accomplished by the inventor, utilizing the method of division. Under careful observation 'ORKNEY CHERRY' has been determined stable, uniform, and reproduces true to type in successive generations of asexual propagation.

SUMMARY OF THE INVENTION

The following traits have been repeatedly observed and represent the distinguishing characteristics of the new *Geranium* variety 'ORKNEY CHERRY'. The traits in combination distinguish 'ORKNEY CHERRY' from all other varieties of *Geranium* known to the inventor. The new invention has not been tested under all possible conditions and phenotypic differences may be observed with variations in environmental, climatic, and cultural conditions, however, without any variance in genotype.

1. 'ORKNEY CHERRY' exhibits low compact spreading habit.
2. 'ORKNEY CHERRY' exhibits bright fuchsia-red flowers.
3. 'ORKNEY CHERRY' exhibits dark purple-green foliage.
4. 'ORKNEY CHERRY' blooms in spring, summer, and fall.
5. 'ORKNEY CHERRY' is 12 cm. in height and 23 cm. in diameter at maturity.
6. 'ORKNEY CHERRY' is asexually propagated by the methods of softwood cuttings and division.
7. Cultural requirements for 'CHERRY ORKNEY' are freely-draining soils, full sun, and adequate but not excess water.
8. 'ORKNEY CHERRY' is hardy to USDA Zone 5.
9. 'ORKNEY CHERRY' is not susceptible to any pests or disease known to the inventor.

BRIEF DESCRIPTION OF THE DRAWINGS

The accompanying color drawings illustrate the overall appearance of the new *Geranium* variety named 'ORKNEY CHERRY' showing the colors as true as is reasonably possible to obtain in colored reproductions of this type. The plants in the drawings are 5-month-old and grown out-of-doors in Arroyo Grande, Calif.

The drawing labeled

The drawing labeled

Figure 1:
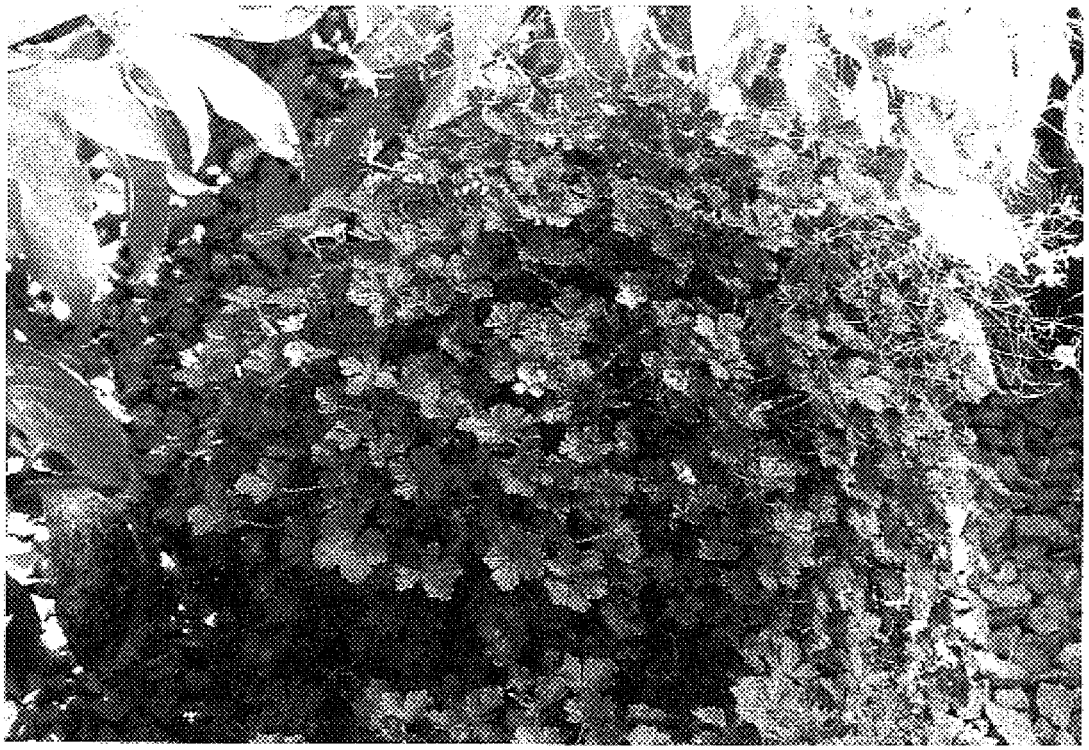
FIG. 1 depicts a view from a side perspective illustrating plant habit.
Figure 2:
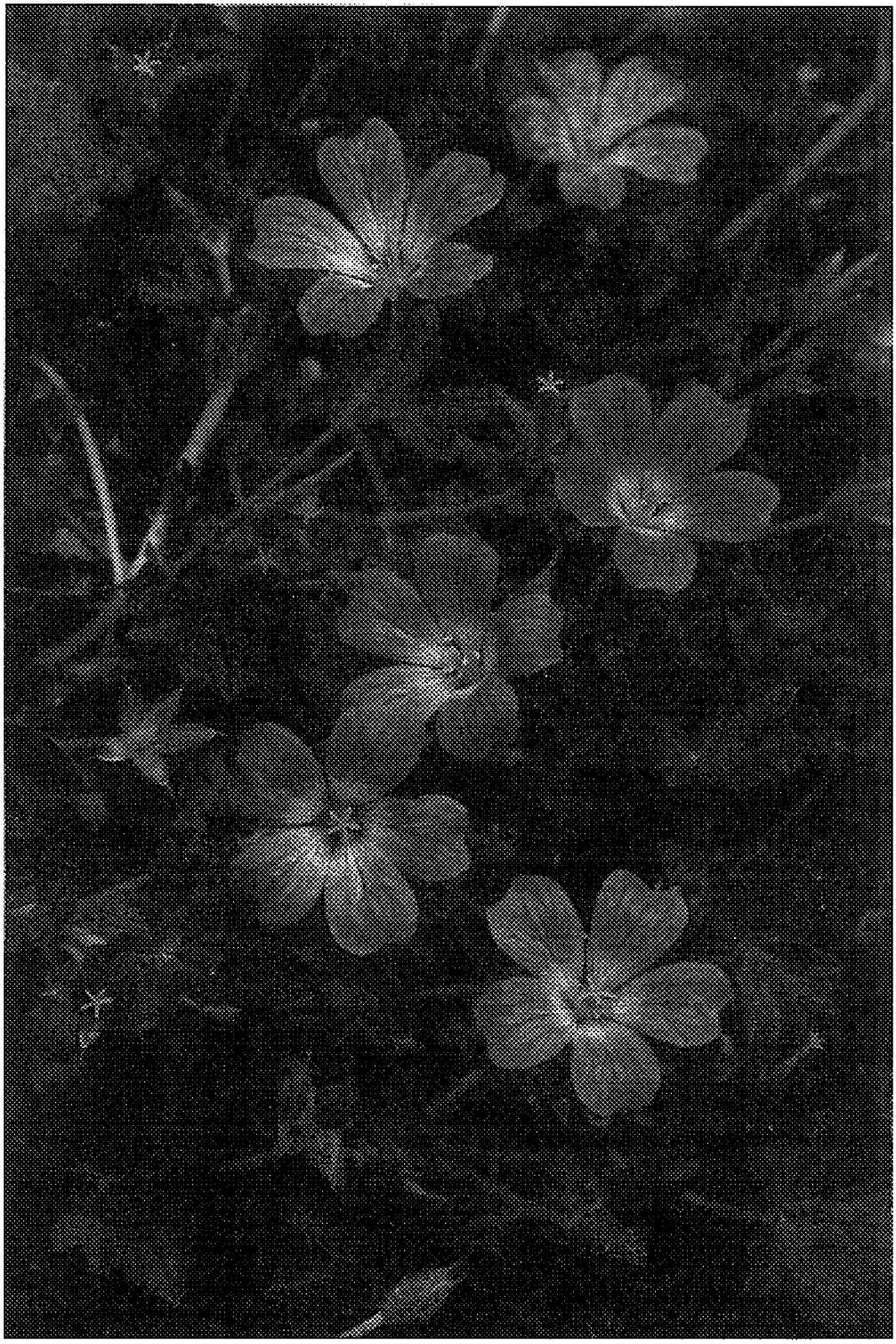
FIG. 2 depicts a close-up view of the flower and foliage. Colors in the photographs may differ from the values cited in the detailed botanical description, which accurately describe the actual colors of the new *Geranium* variety named 'ORKNEY CHERRY'.

All photographs are taken using conventional photographic techniques and although colors may appear different from actual colors due to light reflectance, they are as possible by conventional photography.

BOTANICAL DESCRIPTION OF THE PLANT

The following is a detailed description of the new *Geranium* cultivar 'ORKNEY CHERRY'. Data was collected in Arroyo Grande, Calif. from 9-month-old plants grown out-of-doors in 1-liter containers. Color determinations are in accordance with the 2001 Royal Horticultural Society Colour Chart of London, England except where general color terms of ordinary dictionary significance are used. The growing requirements are similar to the species.

Botanical classification: *Geranium×hybrida* 'ORKNEY CHERRY'.
Family: Geraniaceae.
Genus: *Geranium.*
Species: *×hybrida.*
Denomination: 'ORKNEY CHERRY'.
Common name: Cranesbill.
Parentage: *Geranium×hybrida* 'ORKNEY CHERRY' is a seeding selection arising from the deliberate cross-pollination of the following parents:
- *Female parent.*—An individual unnamed seedling of *Geranium×antipodeum.*
- *Male parent.*—An individual unnamed seedling of *Geranium×oxonianum.*

Plant type: Perennial.
Plant use: Border, rock garden, container or groundcover for the landscape.
Plant vigor: Moderate.
Root system: Fine and fibrous roots.
Plant habit: Low, compact and spreading.
Plant dimensions: 12 cm. in height and 23 cm. in diameter in a 1-liter container.
Plant hardiness: USDA Zone 5.
Seasonal interest: Bright fuchsia-red flowers spring, summer, and fall.
Asexual propagation method: Softwood cuttings and division.
Special needs: Cut back after flowering to induce fresh flush of foliage and flowers.
Cultural requirements: Freely-draining soils, full sun, and adequate but not excess water.
Rooting time: A range of 4–6 weeks.
Crop time: A range of 4–6 months is needed to produce a finished 1-liter commercial container plant from a rooted cutting.
Susceptibility or resistance to pests and disease: No known susceptibility or resistance to pests or diseases known to the inventor.
Stem:
- *Branching pattern.*—Rosette.
- *Stem shape.*—Cylindrical.
- *Stem color.*—146C.
- *Stem surface.*—Pubescent.
- *Stem length.*—Average of 11 cm.
- *Stem diameter.*—Average of 3 mm.

Foliage:
- *Leaf arrangement.*—Opposite.
- *Leaf division.*—Palmate.
- *Leaf shape.*—Reniform.
- *Leaf base.*—Auriculate.
- *Leaf apex.*—Rounded apex.
- *Leaf margin.*—Palmatifid margin.
- *Leaf color* (*adaxial surface*).—Combination of colors N187A and 146A.
- *Leaf color* (*abaxial surface*).—146B.

*Leaf surface* (*adaxial and abaxial surfaces*).—Pubescent.
*Leaf appearance* (*adaxial and abaxial surfaces*).—Matte appearance.
*Leaf length.*—Ranges from 1 cm. to 3 cm. in length.
*Leaf width.*—Ranges from 1 cm. to 3.50 cm. in width.
*Leaf venation.*—Pinnipalmate.
*Vein color* (*adaxial surface*).—187A.
*Vein color* (*abaxial surface*).—146C.
*Leaf attachment.*—Petiolate.
*Petiole length.*—Ranges from 2.50 cm. to 7 cm.
*Petiole diameter.*—2.50 mm.
*Petiole shape.*—Cylindrical.
*Color of petiole.*—146C.
*Petiole surface.*—Pubescent.
*Stipules.*—None observed.
*Foliar fragrance.*—None observed.

Flower:
*Inflorescence.*—Umbel.
*Flower quantity.*—2 flowers per inflorescence.
*Flower arrangement.*—Cymule.
*Flower shape.*—Rotate.
*Flower dimensions.*—1.75 cm. in diameter and 1 cm. in depth.
*Aspect.*—Facing upward and outward.
*Self-cleaning or persistent.*—Self-cleaning.
*Flower color.*—N74A.
*Petals.*—Five in number.
*Petal dimensions.*—0.75 cm. in length and 0.50 cm. in width.
*Petals fused or unfused.*—Unfused.
*Petal margin.*—Entire.
*Petal apex.*—Emarginate.
*Petal base.*—Cuneate.
*Petal shape.*—Obcordate.
*Petal surface* (*abaxial and adaxial surfaces*).—Glabrous.
*Petal color* (*adaxial surface*).—N74A.
*Petal color* (*abaxial surface*).—N74B.
*Peduncle shape.*—Cylindrical.
*Peduncle surface.*—Pubescent.
*Peduncle length.*—Ranges from 2.75 cm. to 5 cm.
*Peduncle width.*—1.50 mm.
*Peduncle color.*—146A.
*Pedicel shape.*—Cylindrical.
*Pedicel surface.*—Lanate.
*Pedicel colour.*—146C.
*Pedicel dimensions.*—9 mm. in length and 1.50 mm. in diameter.
*Stipules.*—3 in number.
*Stipule dimensions.*—5 mm. in length and 1 mm. in width.
*Stipule surface.*—Pubescent.
*Stipule shape.*—Ensiform.
*Stipule apex.*—Acuminate.
*Stipule base.*—Truncate.
*Stipule colour.*—146D.
*Bud color.*—N74A and 146A.
*Bud shape.*—Ovoid.
*Bud surface.*—Villous.
*Bud dimensions.*—7 mm. in length and 5 mm. in width.
*Bud apex.*—Rounded.
*Calyx shape.*—Stellular.
*Calyx diameter.*—0.75 cm.
*Sepals.*—5 in number.
*Sepal dimensions.*—7 mm. in length and 2 mm. in width.
*Sepal margin.*—Entire.
*Sepal surface.*—Villous.
*Sepal shape.*—Ovate.
*Sepals fused or unfused.*—Unfused.
*Sepal apex.*—Caudate.
*Sepal base.*—Truncate.
*Sepal color* (*adaxial and abaxial surfaces*).—146A.
*Flower fragrance.*—None observed.

Reproductive organs:
*Stamens.*—Eight stamens united at base.
*Stamen color.*—155A.
*Stamen length.*—1 mm. in length.
*Pistil.*—One in number.
*Pistil shape.*—Urn-shaped.
*Pistil color.*—155A.
*Pistil height.*—3 mm. in height.
*Pollen quantity.*—Minimal.
*Pollen color.*—164 D.
*Anther color.*—164D.
*Stigma shape.*—5-pronged.
*Stigma color.*—185D.
*Stigma dimensions.*—2 mm. in diameter.
*Ovary position.*—Superior.
*Ovary color.*—146B.
*Ovary shape.*—Ovoid in shape.
*Ovary dimensions.*—2.50 mm. in height and 2 mm. in width.

Seed: No seed has been observed to date.

It is claimed:

1. A new and distinct variety of *Geranium* plant named 'ORKNEY CHERRY' as described and illustrated herein.

* * * * *